United States Patent
Suh et al.

(10) Patent No.: US 9,005,636 B2
(45) Date of Patent: Apr. 14, 2015

(54) PHARMACEUTICAL COMPOSITION COMPRISING METFORMIN AND ROSUVASTATIN

(75) Inventors: Hearan Suh, Seoul (KR); Taekun An, Yongin (KR); Juhuen Choi, Seoul (KR); Choongho Ryu, Suwon (KR); Gughwan An, Gunpo (KR)

(73) Assignee: BCWorld Pharm Co., Ltd., Yeoju-Gun, Gyeonggi-Do (KR)

( * ) Notice: Subject to any disclaimer, the term of this patent is extended or adjusted under 35 U.S.C. 154(b) by 31 days.

(21) Appl. No.: 13/520,320

(22) PCT Filed: Dec. 30, 2010

(86) PCT No.: PCT/KR2010/009606
§ 371 (c)(1),
(2), (4) Date: Oct. 22, 2012

(87) PCT Pub. No.: WO2011/081493
PCT Pub. Date: Jul. 7, 2011

(65) Prior Publication Data
US 2013/0035316 A1    Feb. 7, 2013

(30) Foreign Application Priority Data
Dec. 30, 2009   (KR) .................. 10-2009-0134705

(51) Int. Cl.
A61K 9/28    (2006.01)
A61K 9/20    (2006.01)
A61K 9/24    (2006.01)
A61K 31/155  (2006.01)
A61K 31/505  (2006.01)
A61K 45/06   (2006.01)
A61K 9/50    (2006.01)
A61K 9/16    (2006.01)

(52) U.S. Cl.
CPC ............. *A61K 9/2866* (2013.01); *A61K 9/2054* (2013.01); *A61K 9/2095* (2013.01); *A61K 9/1611* (2013.01); *A61K 9/1652* (2013.01); *A61K 9/2009* (2013.01); *A61K 9/205* (2013.01); *A61K 9/209* (2013.01); *A61K 31/155* (2013.01); *A61K 31/505* (2013.01); *A61K 45/06* (2013.01); *A61K 9/5084* (2013.01)

(58) Field of Classification Search
CPC .................... A61K 9/2054; A61K 9/2095
See application file for complete search history.

(56) References Cited

U.S. PATENT DOCUMENTS

| | | |
|---|---|---|
| 2003/0171407 A1 | 9/2003 | Freese et al. |
| 2004/0002519 A1 | 1/2004 | Damon et al. |
| 2006/0240095 A1 | 10/2006 | Junien et al. |
| 2007/0196480 A1 | 8/2007 | Woo et al. |
| 2008/0249156 A1 | 10/2008 | Palepu |

FOREIGN PATENT DOCUMENTS

| | | |
|---|---|---|
| CN | 1838949 A | 9/2006 |
| EP | 2519240 A1 * | 12/2010 |
| KR | 10-2006-0096728 A | 9/2006 |
| WO | 2005-084666 A1 | 9/2005 |
| WO | 2008-156561 A1 | 12/2008 |

OTHER PUBLICATIONS

Office Action for Chinese Application No. 201080063759.4, from The State Intellectual Property Office of China, issued Mar. 25, 2013.
Hanai, Jun-ichi et al., The muscle-specific ubiquitin ligase atrogin-1/MAFbx mediates statin-induced muscle toxicity, The Jrl of Clinical Investigation, vol. 117, No. 12 (Dec. 2007) pp. 3940-3951.
Office Action for Japanese Patent Application No. 2012-547034, mailed Nov. 12, 2013.
International Search Report for PCT/KR2010/009606 dated Sep. 21, 2011.
Japanese Office Action mailed May 13, 2014, in corresponding Japanese Patent Application No. 2012-547034 (with English translation).
Extended European Search Report for European Patent Application No. 10841325, dated Feb. 21, 2014, 8 pages.
Office Action from Korean Intellectual Patent Office for Korean Patent Application No. 10-2012-7020145, dated Jan. 21, 2014.
Office Action for Chinese Application No. 201080063759.4, from The State Intellectual Property Office of China, issued Mar. 6, 2014.

* cited by examiner

*Primary Examiner* — Carlos Azpuru
(74) *Attorney, Agent, or Firm* — Mintz Levin Cohn Ferris Glovsky and Popeo, P.C.; Kongsik Kim (57) ABSTRACT

This invention relates to oral pharmaceutical compositions of metformin and rosuvastatin. In detail, a pharmaceutical composition comprising metformin, rosuvastatin, sustained release carriers and/or excipients reduces the side effects caused by statins and enhances safety, patients' convenience and compliance with its one-per-day dosage. In addition, regulation of an early effective blood concentration of the drug and maintenance of the drug's concentration at a steady level in vivo by a controlled-release can be advantageously used as a pharmaceutical composition for preventing and treating hyperlipidemia.

7 Claims, 5 Drawing Sheets

PHARMACEUTICAL COMPOSITION COMPRISING METFORMIN AND ROSUVASTATIN

CROSS-REFERENCES TO RELATED APPLICATIONS

This application is a U.S. national phase application, pursuant to 35 U.S.C. §371, of PCT/KR2010/009606, filed Dec. 30, 2010, designating the United States, which claims priority to Korean Application No. 10-2009-0134705 filed Dec. 30, 2009. The entire contents of the aforementioned patent applications are incorporated herein by this reference.

TECHNICAL FIELD

The present invention relates to an oral pharmaceutical composition of metformin and rosuvastatin. In detail, this invention comprising metformin, rosuvastatin, sustained release carriers and/or excipients reduces side effects caused by statins and enhances safety, patients'convenience and compliance with its one-per-day dosage. In addition, regulation of an early effective blood concentration of the drug and maintenance of the drug's concentration at a steady level in vivo by a controlled-release can be advantageously used as the pharmaceutical composition for preventing and treating hyperlipidemia.

BACKGROUND ART

1. U.S. Pat. No. 6,858,618
2. *Am J. Cardiol*, 102, pp. 1654-1662, 2008
3. *Life Science*, 82, pp. 969-975, 2008
4. *J. Clin. Ivest.*, 117, pp. 3940-3951, 2007
5. *Proc. Nat. Acad. Sci.*, 103(44), pp. 16260-16265, 2006

DISCLOSURE OF INVENTION

Technical Problem

Hyperlipidemia comes with an array of diseases caused by an abnormal surge in lipid components in blood plasma such as cholesterol, triglyceride and so forth. Hyperlipidemia or an increase of lipid in blood plasma relates to the frequency of developing both cardiovascular diseases and hardening of the arteries. In detail, hypercholesterolemia works as a primary risk factor in developing and stimulating atherosclerosis and hypertriglyceridemia causes pancreatitis.

In general, statin lipid-lowering drugs are used as first-in-class drugs to prevent and treat heart diseases caused by coronary sclerosis such as angina pectoris and cardiac infarction. For instance, rosuvastatin, as a 3-hydroxy-3-methylglutaryl-CoA (HMG-CoA) reductase inhibitor (USP) which regulates the synthetic pathway of cholesterol, has an effect of lowering the level of cholesterol, LDL-cholesterol and triglyceride which are increased by mainly primary hypercholesterolemia and mixed dyslipidemia, and simultaneously incrementing the level of HDL-cholesterol.

Rosuvastatin decreases the level of LDL-cholesterol and triglyceride and increases HDL more than other existing statins. However, it affects myotoxicity followed by a decline in precursors of CoQ10, dolichols and isoprenoids as well as low cholesterol level during the rate-limiting step of synthesizing cholesterol, which deters the synthesis of mevalonate and it finally causes severe side effects such as myalgia, muscle cell damage and rhabdomyolysis (Am J. Cardiol, 102, pp. 1654-1662, 2008; Life science, 82, pp. 969-975, 2008).

However, a recent study has revealed that rhabdomyolysis, the well-known symptom of statins including rosuvastatin, is related to ligase atrogin-1 alpha. Specifically, muscle proteins are broken down through cellular mechanism with the activity of UPP (ubiquitin proteasome pathway). Atrogin-1 (MAFbx:Muscle atrophy F-box) as ubiquitin-protein ligase E3 and another ligase MURF1 (Muscle RING Finger 1) are the elements forming UPP and inducing muscular atrophy. Among them, atropin-1 is proven to be induced in the early stage of muscular atrophy and increases prior to a diminution in muscle mass. For instance, a mouse deprived of atrogin-1 has resistance to muscular atrophy, which indicates that atropin-1 destroys key proteins of muscle (J. Clin. Nest., 117, pp. 3940-3951, 2007).

Atrogin-1 is known to be closely connected with PGC-1 alpha which is known to be a transcriptional co-activator involved in physiological reactions associated with homeostasis of muscle and other tissues, temperature regulation and glycometabolism (J. Clin. Ivest., 117, pp. 3940-3951, 2007; Proc. Nat. Acad. Sci., 103(44), pp. 16260-16265, 2006).

The result that PGC-1 alpha lessens skeletal muscle damage caused by statins means that the number and the function of mitochondria play a critical role to the whole muscle. To explain the activation phase of PGC-1 alpha, activated AMPK enzyme transports glucose transporter proteins with microsomes in cells to the muscle cell membrane, leading to a rise in GLUT-4 (glucose transporter-4). In the end, P38 MAPK goes through the phosphate pathway and finally PGC-1 gets activated.

Activated PGC-1 alpha becomes Fox0-dephosphorylated through IGF-1 (insulin-like growth factor-1)/PI3K/AKT signal system, inhibiting nuclear localization and the transcription of atrogin-1. In other words, it is expected that excessive expression of PGC-1 alpha lowers the expression of atrogin-1, preventing muscle damage. The case of C2C12 myotubes shows that the expression of PGC-1 is reduced to that of atrogin-1 alpha (J. Clin. Ivest., 117, pp. 3940-3951, 2007).

To activate AMPK, which is closely connected to PGC-1 alpha activation, there is drug called metformin. Metformin is chemically classified as biguanide and its average dosage is 2,500 mg a day at a maximum, and the correct dosage is 500 mg or 750 mg tablets 2 or 3 times daily with meals. When it is used for patients with diabetes as a non-insulin-dependent diabetes treatment, their blood sugar is regulated by inhibiting the production of glucose.

But until now, there have been no reports related to the pharmaceutical composition of the present invention, the oral pharmaceutical composition, comprising metformin and rosuvastatin, which reduces side effects caused by statins, enhances safety, patients'convenience and compliance with its one-per-day dosage, regulates an early effective blood concentration of the drug and serves as a controlled-release composition, maintaining the drug's concentration at a steady level in vivo, which is so stably effective that it is useful for preventing and treating hyperlipidemia.

While the inventors of this invention were conducting research for the pharmaceutical composition, they affirmed that this pharmaceutical composition comprising metformin and rosuvastatin reduces statins-caused side effects, enhances safety, patients' convenience and compliance with its one-per-day dosage, regulates an early effective blood concentration of the drug and serves as a controlled-release composition, maintaining the drug's concentration at a steady level in vivo, which has a stable effect. They finally completed the pharmaceutical composition for preventing and treating hyperlipidemia.

Solution to Problem

In order to achieve the above objectives, the present invention provides a pharmaceutical composition comprising metformin (therapeutically effective amount of metformin or its pharmaceutically acceptable salts) and rosuvastatin (therapeutically effective amount of rosuvastatin or its pharmaceutically acceptable salts) with the effect of deterring side effects of rosuvastatin, preventing and treating hyperlipidemia.

In one embodiment, the present invention provides the pharmaceutical composition comprising (a) therapeutically effective amount of metformin or its pharmaceutically acceptable salts, (b) sustained release carriers and (c) therapeutically effective amount of rosuvastatin or its pharmaceutically acceptable salts.

In another embodiment, the present invention provides the pharmaceutical composition comprising (a) therapeutically effective amount of metformin or its pharmaceutically acceptable salts, (b) sustained release carriers, (c) therapeutically effective amount of rosuvastatin or its pharmaceutically acceptable salts and (d) excipients.

The term, "pharmaceutically acceptable salts of metformin" defined herein includes, but is not limited to, every salt of metformin which is pharmaceutically acceptable, preferably, metformin HCl, metformin acetyl salicylic acid, metformin fumarate, metformin succinate, metformin maleate, metformin malonate, etc., more preferably, metformin HCl.

The term, "pharmaceutically acceptable salts of rosuvastatin" defined herein includes, but is not limited to, every salt of rosuvastatin which is pharmaceutically acceptable, preferably, rosuvastatin calcium, rosuvastatin HCl, rosuvastatin acetyl salicylic acid, rosuvastatin fumarate, rosuvastatin succinate, rosuvastatin maleate, rosuvastatin malonate, etc., more preferably, rosuvastatin calcium.

The term, "side effect" defined herein includes, but is not limited to, those caused by statins, preferably muscle pain, muscle cell damage, rhabdomyolysis and so on, more preferably, rhabdomyolysis.

The term, "sustained release carrier" defined herein includes, but is not limited to, those carriers lessening the side effects caused by a surge in blood concentration and maintaining correct timing of its sustained release. One or more carriers are selected among the following; hydroxy propyl methyl cellulose, sodium carboxyl methyl cellulose, methyl cellulose, ethyl cellulose, hydroxy methyl cellulose, hydroxy ethyl cellulose, hydroxy propyl cellulose, hydroxy ethyl methyl cellulose, hydroxy ethyl ethyl cellulose, hydroxy propyl ethyl cellulose, alkyl hydroxy propyl methyl cellulose, polyethylene oxide, polyvinyl acetate, polyvinyl alcohol, povidone and its derivatives, corn starch, potato starch, pregelatinized starch and its derivatives, hydroxy ethyl starch, dextrin and its derivatives, dextran, maltodextrin, polydextrose, alginic acid or its derivatives, guar gum, locust bean gum, xanthan gum, cyclodextrin, arabia gum, gellan gum, karaya gum, casein, tara gum, tamarind gum, tragacanth gum, ghatti gum, gelatin, collagen, protamine, zein, carbomer, polyacrylamide, poly vinyl acetal diethyl amino acetate, glucomannan, glucosamine, arabinogalactan, furcelleran, pullulan, polyurethane, chitosan, chitin, agar, pectin, carrageenan, preferably, polyethylene oxide, polyvinyl acetate, polyvinyl alcohol, povidone, methyl cellulose, ethyl cellulose, hydroxy methyl cellulose, hydroxy ethyl cellulose, hydroxy propyl cellulose, hydroxy ethyl methyl cellulose, hydroxy propyl methyl cellulose, more preferably, hydroxy propyl methyl cellulose, much more preferably, hydroxy propyl methyl cellulose with its strength accounting for about 1%-80% in a Tablet or the product.

The term, "excipient" defined herein as a drug coating layer, simple pharmaceutical composition, or additional matrix layer, includes, but is not limited to, one or more coating material, simple pharmaceutical composition material, additional matrix material and specifically one or more excipients are selected among the following; microcrystalline Cellulose, hydroxy propyl methyl cellulose, sodium carboxyl methyl cellulose, methyl cellulose, ethyl cellulose, hydroxy methyl cellulose, hydroxy ethyl cellulose, hydroxy propyl cellulose, hydroxy ethyl methyl cellulose, hydroxy ethyl ethyl cellulose, hydroxy propyl ethyl cellulose, alkyl hydroxy propyl methyl cellulose, hydroxy propyl methyl cellulose phthalate, hydroxy propyl methyl cellulose acetate succinate, cellulose acetate, cellulose acetate phthalate, polyethylene oxide, polyvinyl acetate, polyvinyl alcohol, povidone and its derivatives, corn starch, potato starch and pregelatinized starch and its derivatives, hydroxy ethyl starch, dextrin and its derivatives, dextran, maltodextrin, polydextrose, guar gum, locust bean gum, xanthan gum, cyclodextrin, arabia gum, gellan gum, karaya gum, casein, tara gum, tamarind gum, tragacanth gum, ghatti gum, gelatin, collagen, protamine, carbomer, poly acryl amide, carnauba wax, beeswax, sucrose, liquid sucrose, lactose, polyvinyl acetate, diethyl aminoacetate, additionally, polyurethane, chitosan, chitin, agar, pectin, carrageenan or shellac, preferably, polyvinyl acetate, cellulose acetate, povidone, hydroxy propyl methyl cellulose or polyvinyl alcohol, more preferably, hydroxy propyl methyl cellulose or polyvinyl alcohol, much more preferably, hydroxy propyl methyl cellulose or polyvinyl alcohol with its strength accounting for 0.01%-50% in a Tablet.

Examples of the manufacturing process are described below:

Step (1) is producing dried granules after mixing metformin, sustained release carriers and/or excipients Step (2) is preparing tablets with the mixed granules of step (1), excipients and/or active ingredients (rosuvastatin or rosuvastatin dried granules).

Step (3) is coating the tablets of step (2) with coating agent and/or active ingredients (rosuvastatin or rosuvastatin dried granules).

Step (4) is additionally coated tablet of step (3) with film forming excipients.

Through the aforementioned process, the present invention, "the pharmaceutical composition comprising metformin and rosuvastatin" can be prepared.

This invention relates to the oral pharmaceutical composition whose active ingredients are metformin and rosuvastatin, reducing the side effects caused by statins, enhancing safety, patients' convenience and compliance with its one-per-day dosage. In addition, it regulates an early effective blood concentration of the drug and serves as a controlled-release composition, maintaining the drug's concentration at a steady level in vivo, which has a stable effect.

The ingredients of the product and the principles of the present invention are described and characterized in more detail hereinafter.

The product of the present invention contains metformin, one of biguanides, and rosuvastatin, an 3-hydroxy-3-methyl-glutaryl-CoA (HMG-CoA) reductase inhibitor, as pharmacologically active ingredients, specifically, the product is administered once a day.

Among those main ingredients of the pharmaceutical composition, the effective dose of rosuvastatin ranges from about 1 mg to 100 mg, preferably, about 3 mg to 50 mg, more preferably, about 5 mg to 30 mg. That of metformin ranges from about 100 mg to 2500 mg, preferably, about 150 mg to 1500 mg, more preferably, about 200 mg to 1100 mg. Much more preferably, on the effective dose of rosuvastatin/metformin basis, the following dose is administered once a day; 5 mg/250 mg, 5 mg/500 mg, 5 mg/1000 mg, 10 mg/250 mg, 10 mg/500 mg, 10 mg/1000 mg, 20 mg/250 mg, 20 mg/500 mg, 20 mg/1000 mg.

In a preferred embodiment, a feature is that the mixing ratio of the mixture of (a) metformin (therapeutically effective amount of metformin or its pharmaceutically acceptable salts), (b) sustained release carriers and (c) rosuvastatin (therapeutically effective amount of rosuvastatin or its pharmaceutically acceptable salts) is 1:0.01~5:0.001~0.5, preferably, 1:0.05~2:0.005~0.025; that of (a) metformin (therapeutically effective amount of metformin or its pharmaceutically acceptable salts), (b) sustained release carriers, (c) rosuvastatin (therapeutically effective amount of rosuvastatin or its pharmaceutically acceptable salts) and (d) excipients is 1:0.01~5:0.001~0.5:0.01~5, preferably, 1:0.05~2:0.005~0.025:0.005~0.025.

A feature of the pharmaceutical composition of the present invention is that metformin shows sustained release patterns where it is constantly eluted in water or physiological pH dissolution medium for about 2 to 24 hours, preferably, about 4 to 20 hours, more preferably, about 6 to 16 hours or more; rosuvastatin shows immediate release patterns or sustained release patterns. When it shows immediate release patters, 50 to 100%, or preferably, 70 to 90% of it is eluted in water or physiological pH dissolution medium for approximately 10 to 60 minutes, preferably about 20 to 50 minutes, more preferably, about 25 to 40 minutes. When it shows sustained release patterns, it is constantly released for about 1 to 24 hours, preferably, about 4 to 20 hours, and more preferably, about 6 to 16 hours or more.

The pharmaceutical composition of the present invention comprising metformin and rosuvastatin as active ingredients, has an effect of inhibiting side effects, controlling the release upon its administration and maintaining the elution rate of the drug at a stable level when it is administered by simultaneously using active ingredients, sustained release carriers and excipients.

Carriers, excipients and diluents which can be included in the composition of the present invention as a part can be selected among lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinyl pyrrolidone, water, methyl hydroxy benzoate, propyl hydroxy benzoate, talc, magnesium stearate and mineral oil. When it is formulated, it is prepared using propellants, bulking formulations, binders, humectants, disintegrants, diluents such as surfactants, or excipients.

The preferable dose of the pharmaceutical composition of the present invention depends on patients' condition and weight, the status of diseases, the type of drug, the pathway of administration and the period but, it can be properly selected by the person of ordinary skill in the pertinent art.

The ingredients and the principles of the pharmaceutical composition of the present invention comprising metformin and rosuvastatin are described in more detail hereinafter.

The examples of the manufacturing procedure of this pharmaceutical composition comprise the steps of:

The first step (a) is manufacturing dried granules after mixing with proper ratio of (1) metformin and (2) one or more sustained release carriers selected among the group of carriers that are pharmaceutically acceptable such as sodium carboxyl methyl cellulose, methyl cellulose, ethyl cellulose, hydroxy methyl cellulose, hydroxy ethyl cellulose, hydroxy propyl cellulose, hydroxy ethyl methyl cellulose, hydroxy propyl methyl cellulose, etc.

The second step (b) is adding excipients and/or active ingredients (rosuvastatin or rosuvastatin dried granules) to granules from the first step (a) and manufacturing tablets with a tablet press.

The third step (c) is coating the tablets from the second step (b), with coating agents and/or active ingredients (rosuvastatin or rosuvastatin dried granules).

The last step (d) provides the manufacturing method of the pharmaceutical composition of the present invention including the process of final film coating of the tablets coated in the third step (c).

Every procedure involved in the manufacturing of the pharmaceutical composition of the present invention can be conducted according to the typical process.

Pharmaceutically acceptable excipients can be added during the procedure of manufacturing granules (step (a)), the procedure of manufacturing tablets and (step (b)), the mixing procedure (step (c)). Additionally, the forming the film layer on the surface of the tablets (step (d)), can be added to the granules created in step (a), the tablets formed in step (b) and/or the coated tablets in step (c).

Moreover, the present invention provides the manufacturing method of the pharmaceutical composition, which includes the extra step of adding (a) dried granules, manufactured using the process above, (b) the aforementioned sustained release carriers, (c) rosuvastatin (therapeutically effective amount of rosuvastatin or its pharmaceutically acceptable salts)) and (d) pharmaceutically acceptable excipients.

The extra excipients known in the pharmaceutical industry, which can be added to the composition are the following; binders, lubricants, disintegrants, coloring formulations, preservatives, sweeteners, flavors, stabilizers, moisturizers, buffer solution, anti-micro viral formulations, bulking formulations, anti-oxidants or diluents.

One or more binders which can be used in the present invention are additionally selected among the following common binders; preferably water, organic solvents, polyvinyl pyrrolidone, hydroxy propyl cellulose, microcrystalline cellulose, hydroxy propyl methyl cellulose, dextrin, gelatin, methyl cellulose, hydroxy cellulose, hydroxy methyl cellulose, polyvinyl alcohol, pregelatinized starch or arabia gum.

Disintegrants can be selected among the following common disintegrants; preferably sodium starch glycolate, crospovidone, cross-linked sodium carboxylmethyl cellulose, low substituted hydroxy propyl cellulose, hydroxy propyl methyl cellulose, polyvinyl pyrrolidone, starch, carboxyl methyl cellulose calcium and a mixture of them.

Lubricants can be selected among the following common lubricants; preferably magnesium stearate, talc, stearic acid, light anhydrous silicic acid and a mixture of them.

Moisturizers can be selected among the following common moisturizers; preferably polyethylene glycol, chemical compounds whose molecular weight is less than 20,000 with alcohol's hydroxy group in its structure or a mixture of them.

If necessary, one or more of the following coloring formulations can be added to the tablets; titanium dioxide, iron oxide, magnesium carbonate, calcium sulfate, magnesium oxide, magnesium hydroxide, aluminum lake, etc.

One or more preservatives of the present invention can be selected among the following; benzoic acid, methyl paraben or propyl paraben, etc. Aside from these, sweeteners, flavors, stabilizers and diluents can be additionally added.

An array of oral compositions can be prepared, using the pharmaceutical composition of the present invention. For instance, we can manufacture directly compressed tablets, compressed-coated tablets, double-layered tablets and triple-layered tablets, including metformin and rosuvastain as active ingredients and combined with aforementioned excipients that are pharmaceutically acceptable.

Advantageous Effects of Invention

As it is explained above, the oral pharmaceutical composition of the present invention comprising metformin, rosuvastatin, sustained release carriers and/or excipients reduces side effects caused by statins and enhances safety, patients' convenience and compliance with its one-per-day dosage. In addition, regulation of an early effective blood concentration of the drug and maintenance of the drug's concentration at a steady level in vivo by a controlled-release can be advantageously used as the pharmaceutical composition for preventing and treating hyperlipidemia.

BEST MODE FOR CARRYING OUT THE INVENTION

The following description and examples illustrate selected embodiments of the present invention. In light thereof, variations and modifications will be suggested to one skilled in the art, all of which are within the spirit and purview of this invention.

Example 1

Preparation of Sustained Release Granules 1-1. Preparation of Sustained Release Dried Metformin Granules Metformin hydrochloride (Granules, India), hydroxy propyl methyl cellulose 2208 (Metolose 90SH-100000SR, Shin-Etsu Chemical), hydroxy propyl methyl cellulose 2910 (Pharmacoat 603, Shin-Etsu), microcrystalline cellulose (Avicel 102, FMC Biopolymer) and sodium carboxyl methyl cellulose (Blanose 7HF, Aqualon) were mixed in a high speed mixer (SPG-2, Dalton) for 5 minutes; then the mixture generated by wet granulation method were dried for approximately 1 hour in a drying oven at about 50-70° C. and sieved with sieve mesh no. 30. Finally, the mixture were manufactured to dried metformin granules with sustained release according to the composition of Table 1 below.

TABLE 1

| Purpose | Composition | Weight (mg) |
| --- | --- | --- |
| Active ingredient | Metformin hydrochloride | 500 |
| Sustained release carrier | Hydroxy propyl methyl cellulose 2208 | 358 |
| Excipient | Hydroxy propyl methyl cellulose 2910 | 10 |
|  | Microcrystalline cellulose | 102 |
|  | Sodium carboxyl methyl cellulose | 50 |
|  | Magnesium stearate | 10 |
| Total |  | 1030 |

1-2. Preparation of Dried Rosuvastatin Granules

Rosuvastatin calcium (Biocon, India), calcium phosphate (Calipharm T, Innophos), microcrystalline cellulose (Avicel 102, FMC Biopolymer) and lactose (Pharmatose, DMV-Fonterra) were mixed for 5 minutes and sieved with sieve mesh no. 40; and this was mixed with crospovidone (Kollidon CL, BASF) and magnesium stearate (Junsei), which were sieved with sieve mesh no. 30 in a high speed mixer (SPG-2, Dalton) for 5 minutes. Finally, dried rosuvastatin granules were manufactured according to the composition of Table 2 below.

TABLE 2

| Purpose | Composition | Weight (mg) |
| --- | --- | --- |
| Active ingredient | Rosuvastatin calcium | 10.40 |
| Sustained release carrier | Calcium phosphate | 10.90 |
| Excipient | Microcrystalline cellulose | 29.82 |
|  | Lactose | 89.50 |
|  | Crospovidone | 7.50 |
|  | Magnesium stearate | 1.88 |
| Total |  | 150 |

Example 2

Preparation of the Pharmaceutical Composition (1)

2-1. Preparation of the Tablets

The dried metformin granules with sustained release, prepared from Example 1-1, were completely mixed with magnesium stearate (0 mg per tablet, the same amount as in Table 1), which was sieved with seive no. 30; and the mixture was tableted into a tablet using a tablet press (Ek0, Korsch) with an ordinary pressure. Then 100 of white-colored sustained release tablets including metformin 1.030 mg per tablet were manufactured.

2-2. Coating of Tablets

The sustained release tablets prepared from Example 2-1 were put in the coating pan (Hi-coater, Sejong Pharma Tech) and the filled air was maintained at 30 to 45° C. According to the composition of Table 3, rosuvastatin and Opadry (a coating agent with 45.52% of PVA, Colorcon) were suspended in a four-fold amount of water and then performed the suspension was sprayed on to the dried tablets above using a spray operated by the air pressure and it was dried for about 10 minutes. The amount of Opadry (a coating agent with 45.52% of PVA, Colorcon) accounted for 5% of the total amount of the tablet herein. In addition, to ensure the stability of the tablets, additional film-coating procedure can be performed before/after they are coated as above, but it is not conducted herein.

TABLE 3

| Purpose | Composition | Weight (mg) |
|---|---|---|
| Active ingredient | Rosuvastatin calcium | 10.40 |
| Coating agent | Opadry (with 45.52% of PVA) | 52.02 |
| Total | | 62.42 |

Example 3

Preparation of the Pharmaceutical Composition (2)

3-1. Preparation of Double-Layered Tablets

The dried metformin granules with sustained release, obtained from Example 1-1 were completely mixed with magnesium stearate (10 mg per tablet, the same amount as in Table 1) which was sieved with sieve mesh no. 30; and the mixture and dried rosuvastatin granules which were prepared in Example 1-2 were tableted into double-layered tablets with a tablet press (Ek0, Korsch) according to the manufacturing method described in the Korean pharmacopoeia.

3-2. Coating of Tablets

The double-layered tablets, obtained from the aforementioned Example 3-1, were put in the coating pan (Hi-coater, Sejong Pharma Tech) where the filled air was maintained at 30 to 45° C.; and coating agent was prepared according to the composition of Table 4 below; then it was sprayed onto the dried tablets using a spray operated by the air pressure; and it was dried for about 10 minutes at room temperature. The amount of the coating agent was about 4% of the total amount of the tablet.

TABLE 4

| Purpose | Composition | Weight (mg) |
|---|---|---|
| Coating agent | Lactose | 1.80 |
| | Iron oxide | 0.18 |
| | Titanium oxide | 1.06 |
| | Glycerol triacetate | 0.36 |
| | Hypromellose | 1.26 |
| Total | | 150 |

Example 4

Preparation of the Pharmaceutical Composition (3)

4-1. Preparation of Simply Pharmaceutical Composition

The dried metformin granules with sustained release, obtained from Example 1-1 above, were completely mixed with magnesium stearate (10 mg per tablet, the same amount as in Table 1) which was sieved with sieve mesh no. 30; and the mixture was rotated 60 times; then it was rerotated 60 times with dried rosuvastatin granules, obtained from Example 1-2; and then the mixture was tableted into a tablet with average pressure using a tablet press (Ek0, Korsch). Finally the simply pharmaceutical compositions were prepared.

4-2. Coating of Tablets

The tablets, obtained from the aforementioned Example 4-1, were put in the coating pan (Hi-coater, Sejong Pharma Tech) and the filled air was maintained at 20 to 45° C.; and coating agent was prepared according to the composition of Table 4 above; then it was sprayed onto the dried tablets using a spray operated by the air pressure and it was dried for about 10 minutes at room temperature. The amount of the coating agent was about 4% of the total amount of the tablet.

Reference Example 1

Cell Culture

Rat myoblast cell line L6 used herein was obtained from Korean Cell Line Bank. Cells were cultured until the number of cells reached $1\times10^6$ in T-75 flask (BD Biosciences) using DMEM (Dulbecco's Modified Eagle medium) supplemented with 4.5 g/L of D-glucose, L-glutamine, 0.11 g/L of sodium pyruvate and 10% FBS (Fetal bovine serum, Gibco; Invitrogen Corp., CA, USA). To differentiate cells, the medium with 2% HS (Horse serum, Gibco; Invitrogen Corp., CA, USA) was inoculated and the cells were incubated at 37° C. in 5% $CO_2$ incubator (Forma scientific, Germany). The medium was replaced every 2 days and subculture was conducted every 3 to 4 days. In addition, the myoblast cells, used in this experiment, were differentiated up to $0.3\times10^6$ in 6 well plate (BD biosciences) before they were used. After the washing step with PBS (Gibco; Invitrogen Corp., CA, USA), the cells were used for ELISA, MTT and PCR analysis.

Reference Example 2

Preparation for the Experiment 2-1. Reagent

L6 cells (skeletal muscle cells) were purchased from the Korean Cell Line Bank and PGC-1 and Atrogin-1 α antibodies were bought from Santa Cruz Biotechnology (Santa Cruz, Calif., USA) and Abeam (Cambridge science Park, UK), respectively, in addition, goat polyclonal secondary antibody to Rabbit IgG-H&L was also purchased from Abram.

DMEM (Dulbecco's Modified Eagle Medium), which was used for cell culture, was purchased from Invitrogen; and all of trypsin, fetal bovine serum and horse serum were purchased from GenDEPOT; and protein assay reagents were purchased from Bio-rad.

Blocking buffer, TMB solution and stop solution, which were used for ELISA, were bought from GenDEPOT and PBS was purchased from Invitrogen. Immuno 96 well plate was purchased from Nunc (MaxiSorp U16 Nunc, Roskilde, Denmark) and MTT solution for MTT assay was bought from Sigma Aldrich (St. Louis, Mo., USA) and lastly, DMSO was purchased from Invitrogen.

2-2. Equipment Used for the Experiment

Microplate fluorescence Genious (Molercular devices, Austria), centrifuge (Eppendorf), microscope (IS-70, Olympus) and PCR (polymerase chain reaction, Biorad) were used for the experiment.

Reference Example 3

Statistical Analysis

Statistical and comparative analysis was performed employing the GraphPad PRISM statistical package (Version 2.00, Graphpadsoftware Inc., San Diego, USA) and reaffirmed by Turkey's post-hoc test. All data reported are mean±S.D.

Experimental Example 1

Dissolution Test 1-1. Dissolution Test of Tablets (1)

Dissolution tests of rosuvastatin, manufactured from Example 2 to 4, were conducted according to Dissolution Test Method No. 2 (Paddle method) of the Korean Pharmacopoeia, based on the same condition described in Table 5.

TABLE 5

| List | Condition |
|---|---|
| Dissolution tester | DT810 (Jasco) |
| Dissolution medium | Water |
| Temperature of dissolution medium | 37° C. |
| Amount of dissolution medium | 900 mL |
| Paddle speed | 50 rpm |
| Time for sampling | 0.25, 0.5, 1, 1.5, 2, 3, 5, 6, 8, 10 and 12 hours |
| Amount of sample | 10 mL |
| Filtration | 0.45 μm syringe filter |

Assay: To analyze rosuvastatin, sample solution was analyzed according to Table 6, using HPLC (MD-2010 plus, Jasco); and to analyze metformin, sample solution was diluted 20 times and analyzed at 232 nm.

In addition, Comparative example 1 (Product "Crestor®" of Company "AstraZeneca") and Comparative example 2 (Product "Glucophage XR®" of Company "Merck") were conducted under the same conditions as those of the present invention to compare the product of the present invention and its dissolution rate.

TABLE 6

| List | Condition |
|---|---|
| Detector | UV absorption spectrophotometer (wavelength: 242 nm) |
| Column | C18 ODS column |
| Temperature of column | 25° C. |
| Mobile phase | Water:Acetonitrile:Phosphoric acid = 600:400:1 |
| Flow rate | 1 mL/min |
| Injection volume | 100 μL |
| Run time | 17 minutes |

Figure 1:
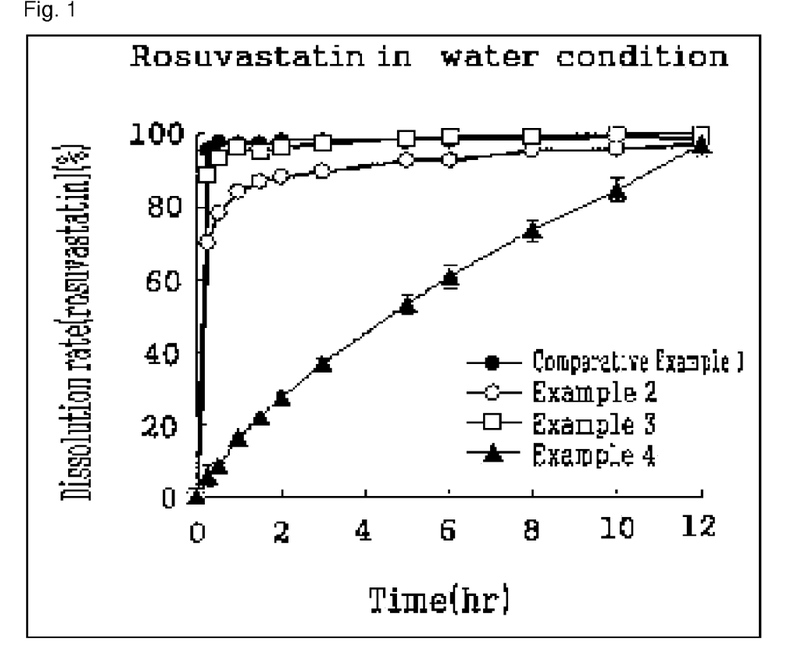
FIG. 1 shows the results of dissolution test of rosuvastatin in Example 2 to 4 and Comparative example 1 (Product "Crestor®" of Company "AstraZeneca").

According to the results shown in Table 7 and FIG. 1, the dissolution rate of rosuvastatin, prepared in Example 2 and 3, showed immediate-release patterns as in Comparative example 1. However, that of rosuvastatin was maintained constantly for 12 hours. It is proven that their sustained release can surpress the abrupt increase of drug plasma concentration in early stage (please refer to Table 7 and FIG. 1).

TABLE 7

| Hour | Comparative example 1 Product "Crestor ®" of Company "AstraZeneca" | Example 2 Rosuvastatin | Example 3 Rosuvastatin | Example 4 Rosuvastatin |
|---|---|---|---|---|
| 0 | 0 | 0 | 0 | 0 |
| 0.25 | 95.51 | 70.46 | 88.91 | 6.01 |
| 0.5 | 97.54 | 78.44 | 93.39 | 8.54 |

TABLE 7-continued

| Hour | Comparative example 1 Product "Crestor ®" of Company "AstraZeneca" | Example 2 Rosuvastatin | Example 3 Rosuvastatin | Example 4 Rosuvastatin |
|---|---|---|---|---|
| 1 | 97.25 | 84.08 | 96.31 | 16.04 |
| 1.5 | 97.28 | 87.05 | 94.93 | 21.86 |
| 2 | 98.29 | 88.18 | 96.22 | 27.39 |
| 3 | 98.28 | 89.80 | 97.41 | 36.74 |
| 5 | 98.01 | 92.76 | 98.59 | 53.25 |
| 6 | 98.16 | 92.79 | 99.01 | 60.65 |
| 8 | 98.07 | 95.34 | 99.27 | 73.70 |
| 10 | 99.45 | 96.14 | 99.87 | 84.81 |
| 12 | 98.66 | 97.50 | 100.00 | 97.48 |

1-2. Dissolution Test of the Tablets (2)

To determine the dissolution rate of metformin in Example 2 to 4, dissolution tests were performed in the same manner as in Experimental Example 1-1.

Figure 2:
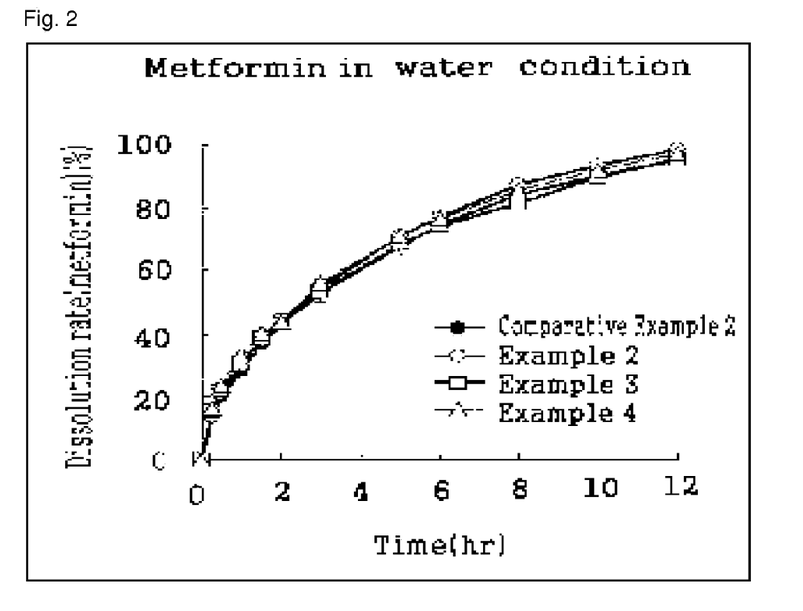
FIG. 2 shows the results of dissolution test of metformin in Example 2 to 4 and Comparative example 2 (Product "Glucophage XR®" of Company "Merck").

The dissolution rate of metfromin in Example 2 to 4 was constant for 12 hours similar to Comparative example 2 (please refer to Table 8 and FIG. 2).

TABLE 8

| Hour | Comparative example 2 Product "Glucophage XR ®" of Company "Merck" | Example 2 Metformin | Example 3 Metformin | Example 4 Metformin |
|---|---|---|---|---|
| 0 | 0 | 0 | 0 | 0 |
| 0.25 | 13.47 | 13.47 | 15.25 | 16.40 |
| 0.5 | 19.73 | 20.73 | 21.69 | 23.41 |
| 1 | 28.27 | 30.80 | 30.66 | 33.14 |
| 1.5 | 36.99 | 38.03 | 38.41 | 40.33 |
| 2 | 42.89 | 44.43 | 43.19 | 44.00 |
| 3 | 52.69 | 54.65 | 53.46 | 56.01 |
| 5 | 68.04 | 71.19 | 68.55 | 71.26 |
| 6 | 74.84 | 77.52 | 74.50 | 76.78 |
| 8 | 84.32 | 87.48 | 81.66 | 85.63 |
| 10 | 90.38 | 93.54 | 89.77 | 92.16 |
| 12 | 95.45 | 98.74 | 95.27 | 97.23 |

Experimental Example 2

Identification of Antibodies by ELISA

To ensure the expression of Atrogin-1 and PGC-1 α in rosuvastatin and metformin, each antibody was treated and analyzed. 100 μL of the serum sample diluted 10 μg/mL in assay diluent buffer were dispensed into each well of 96-well plate (Nunc, Roskilde, Denmark) and incubated at 4° C. overnight ((12 h). Non-bound material was removed after washing four times with phosphate-buffered saline containing 0.2% tween 20 (PBS-T).

The plate was washed 4 times with PBS buffer containing 0.2% Tween 20; and 200 μl of blocking solution (GenDEPOT) containing 1% BSA (Bovine Serum Albumin) with PBS was seeded onto each well and incubated for 2 hours at 4° C.

After washing four times with PBS-T and primary antibody (Abeam) diluted 1:1000 in assay diluent buffer; then each well were tested in volumes of 100 μl per well in duplicate and incubated at room temperature for 4 hours.

After washing four times with PBS-T, 100 μl of Rabbit anti-bovine IgG-HRP diluted 1:1000 in assay diluent buffer was added to all well and the plates were incubated at room-temperature with gentle agitation for 1 hour. 100 μL freshly prepared tetramethyl benzidine (TMB) solution, in 0.1 M sodium acetate buffer pH 6.0, containing 30% $H_2O_2$, was added to each well. After 15 minutes at room temperature, 50 μL of 2M $H_2SO_4$ was added to step the reaction. Lastly, the absorbance was measured at 450 nm using an ELISA reader.

Figure 3:
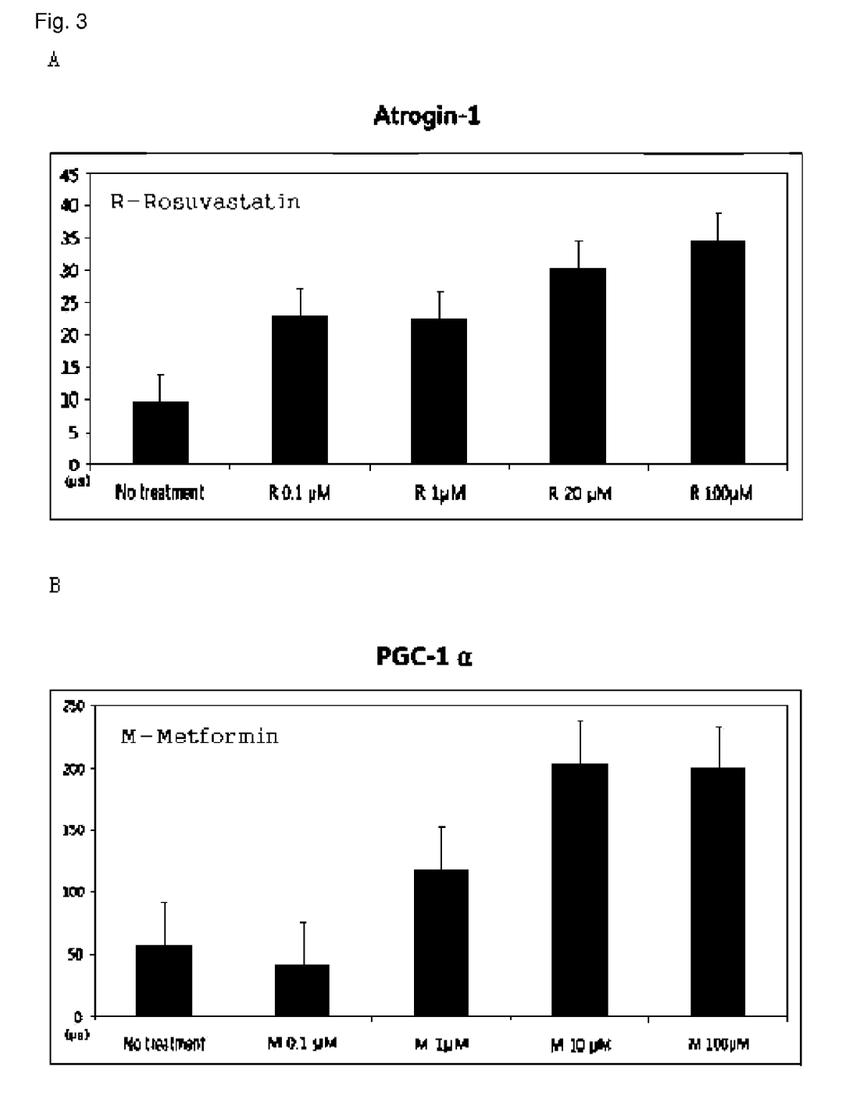
FIG. 3 shows the expression level of Atrogin-1 depending on the concentration of rosuvastatin (A) and the expression level of PGC-1 α depending on the concentration of metformin (B).

As shown in FIG. 3-A, it was found that as the concentration of rosuvastatin was increase the protein expression of Atrogin-1 was increased.

As shown in FIG. 3-B, treating 0.1 μM of metformin did not show a significant difference compared to negative control while treating more than 1 μM of metformin caused an increase in protein level of PGC-1 α (please refer to FIG. 3).

Experimental Example 3

Cell Morphology

Figure 4:
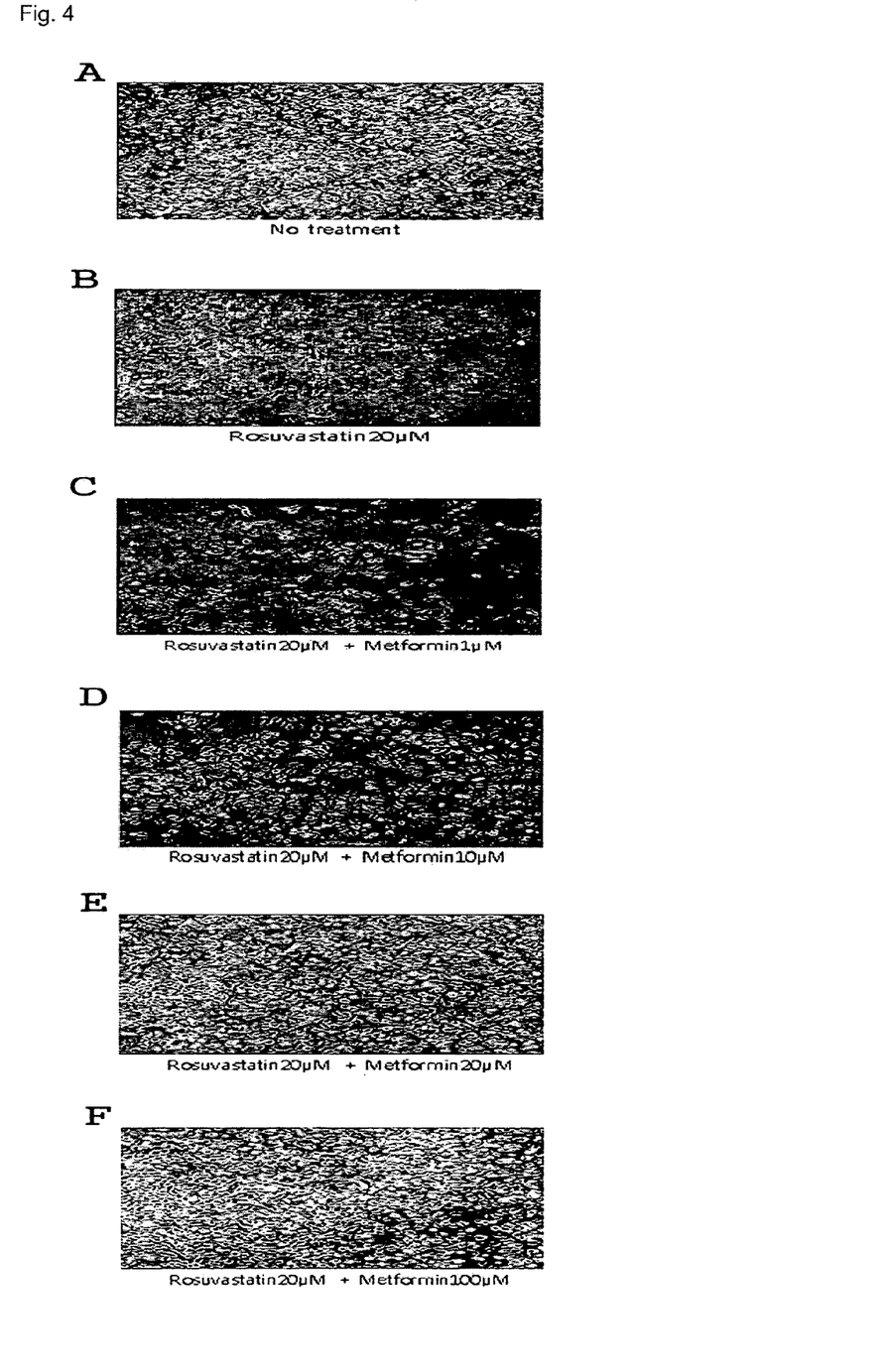
FIG. 4 shows the number of cells when rosuvastatin and/or metformin are treated in rat myoblast cell line L6 in the following manner:
A: a negative control;
B: 20 μM of rosuvastatin;
C: 20 μM of rosuvastatin and 1 μM of metformin;
D: 20 μM of rosuvastatin and 10 μM of metformin;
E: 20 μM of rosuvastatin and 20 μM of metformin; and
F: 20 μM of rosuvastatin and 100 μM of metformin.

To compare the morphology of L6 muscle cells on the concentration of metformin, $0.5 \times 10^5$ muscle cells were seeded onto each well in 6 well plate (Falcon) and incubated at 37° C. in 5% $CO_2$ incubator for 24 hours. 20 μM of rosuvastatin was treated and 0, 1, 10, 20, and 100 μM of metformin was treated, respectively. After 48 hours, all of them were observed using a microscope (IS-70, Olympus), As shown in FIG. 4, the confluence of L6 cells treated with 20 μM of rosuvastatin was decreased significantly compared to the group without treatment. However, the confluence of L6 cells was increased as the concentration of metformin increased. Therefore, it is expected that muscle damage by rosuvastatin will be decreased by adding metformin (please refer to FIG. 4).

Experimental Example 4

MTT Assay

MTT assay was carried out to determine the viability of L6 muscle cells. $1 \times 10^4$ cells were seeded onto each well in 96 well plate and incubated at 37° C. in 5% $CO_2$ incubator for 24 hours.

20 μM of rosuvastatin was treated and 0, 1, 10, 20 and 100 μM of metformin was treated, respectively. They were incubated for 48 hours in the incubator; and each well was treated with 1 mg/1 ml of MTT solution and incubated for 2 hours in the incubator; then each well was treated with DMSO and covered with foil for 10 minutes to dissolve formazan. Lastly, the optical density of formazan was measured at 570 nm using an ELISA Reader.

Figure 5:
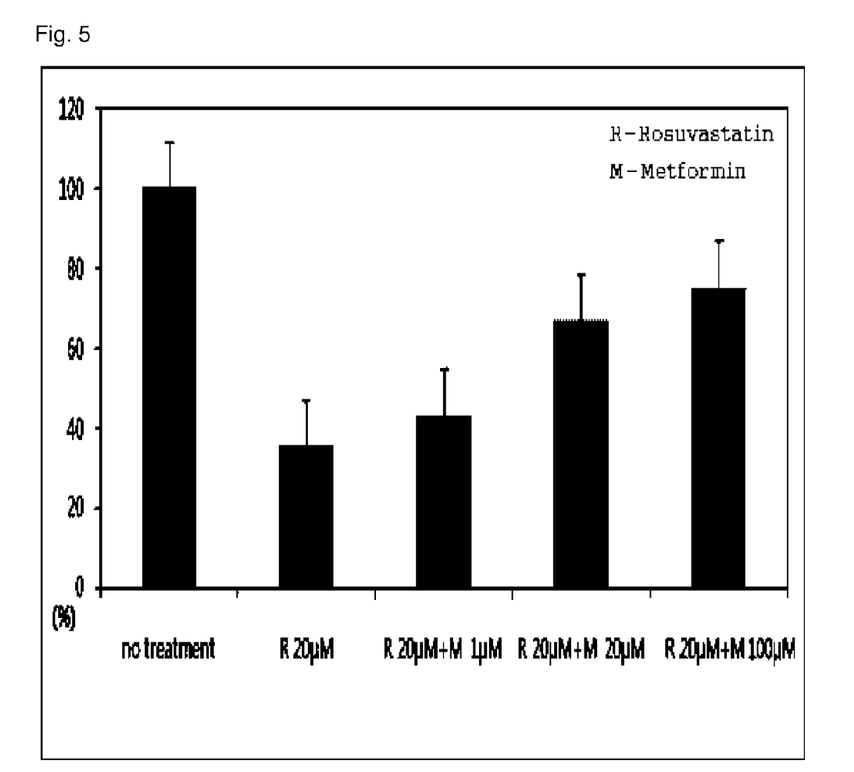
FIG. 5 shows the cell viability in 20 μM of rosuvastatin, and various concentrations of metformin.

As shown in FIG. 5, the group treated with 20 μM of rosuvastatin only showed a significant decrease in the viability of the cells. However, as the concentration of metformin was increased in the combined treatment of rosuvastatin and metformin, the viability of the cells was increased. Specifically, the viability of the group treated with 20 μM of rosuvastatin and 20 μM of metformin increased by 31.6%; and that of 20 μM of rosuvastatin and 100 μM of metformin increased by 39.99% compared to the group with rosuvastatin only. It was suggested that the addition of metformin to rosuvastatin could increase the viability of the cell, resulting in the surpression of cell damage caused by rosuvastatin (please refer to FIG. 5).

Experimental Example 5

RT-PCR (Reverse Transcription)

To measure the mRNA level of Atrogen-1 in muscle cells depending on concentration of metformin, the cells were homogenized in 500 μl of Trizol (Invitrogen) and 3 μg of total RNA was collected using a cell scraper. The total RNA, extracted from muscle cells was put in the mixture of 5× Buffer RT dNTP Mix (5 mM each dNTP) 1.0 μl Rnase inhibitor (10 units/μl) 0.5 μl, Omniscript Reverse Transcriptase 2 units and Rnase-free water (DEPC) 20 μl; and reverse transcription was carried out at 37° C. for 60 minutes and at 72° C. for 1.5 minutes, synthesizing cDNA. Minicycler (Bio-rad, USA) was used for PCR and the synthesized cDNA 3 μl was put in 10× buffer 2 μl (Cosmo-Gentec), dNTP Mix (5 mM each dNTP) 1 μl, Taq DNA polymerase 1 unit (Cosmo-Gentec) 0.3 μl; and each primer (produced by Macrogen) 2 μl and water were added until the total volume reached 20 μl; and amplified.

In PCR, after the initial denaturation was conducted at 96° C. for 3 minutes, 30 cycles of 96° C. for 30 seconds, 55° C. for 30 seconds and 72° C. for 30 seconds were conducted; and the extension was carried out at 72° C. for 5 minutes. In addition, 26 cycles were conducted for β-actin.

The primers used hi RT-PCR are illustrated Table 9 below.

TABLE 9

| Genes | | Oligonucleotide sequence | Size |
|---|---|---|---|
| β-actin | Sense | CGA TTT CCC GCT CGG CCG TGG TGG TGA AGC | 500 bp |
| | Antisense | GGC GAC GAG GCC CAG AGC AAG AGA GGC ATC | |
| PGC-1 α | Sense | CCT GTG GAT GAA GAC GGA TT | 160 bp |
| | Antisense | TAG CTG AGT GTT GGC TGG TG | |
| Atrogin-1 | Sense | TCA CAG CTC ACA TCC CTG AG | 160 bp |
| | Antisense | AGA CTT GCC GAC TCT TTG GA | |

Figure 6:
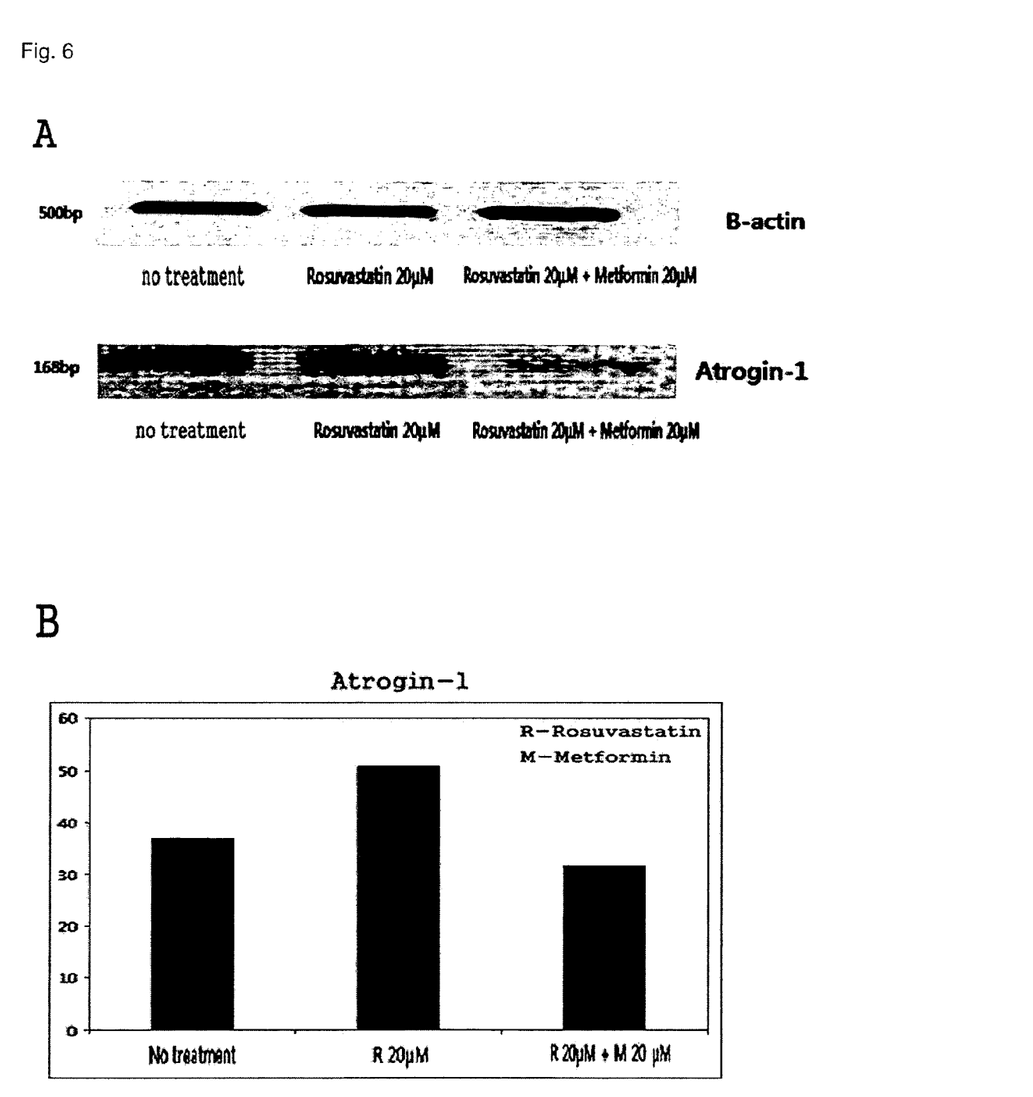
FIG. 6 shows the expression level of Atrogin-1 in negative control, 20 μM of rosuvastatin, and 20 μM of rosuvastatin and 20 μM of metformin.

As shown in FIG. 6, mRNA expression of Atrogin-1 increased in the group treated with 20 μM of rosuvastatin compared to negative control. However, the group treated with 20 μM of rosuvastatin and 20 μM of metformin showed a decrease in mRNA expression of Atrogin-1. Therefore, it is suggested that adding metformin, which was blocked the mRNA expression of Atrogin-1, to rosuvastatin could surpress L6 muscle cell damage caused by rosuvastatin (please refer to FIG. 6).

Mode for the Invention

The present invention related to the Reference examples, Examples and Experimental examples are intended to further illustrate the present invention without limiting its scope.

INDUSTRIAL APPLICABILITY

The present invention relates to the oral pharmaceutical composition of metformin and rosuvastatin. In detail, the invention comprising metformin, rosuvastatin, sustained release carriers and/or excipients reduces side effects caused by statin series medicines and enhances safety, patients' convenience and compliance with its one-per-day dosage. In addition, regulation of an early effective blood concentration of the drug and maintenance of the drug's concentration at a steady level in vivo by a controlled-release, can be applied in the pharmaceutical industry to prevent and treat hyperlipidemia.

The invention claimed is:

1. A tablet comprising: (a) a therapeutically effective amount of metformin or its pharmaceutically acceptable salts, (b) sustained release carriers, (c) therapeutically effective amount of rosuvastatin or its pharmaceutically acceptable salts and (d) excipients, wherein the sustained release carrier is selected from the group consisting of hydroxy propyl methyl cellulose, sodium carboxyl methyl cellulose, methyl cellulose, ethyl cellulose, hydroxy methyl cellulose, hydroxy ethyl cellulose, hydroxy propyl cellulose, hydroxy ethyl methyl cellulose, hydroxy ethyl ethyl cellulose, hydroxy propyl ethyl cellulose, alkyl hydroxy propyl methyl cellulose, polyethylene oxide, polyvinyl acetate, polyvinyl alcohol, povidone and its derivatives, corn starch, potato starch, pregelatinized starch and its derivatives, hydroxy ethyl starch, dextrin and its derivatives, dextran, maltodextrin, polydextrose, alginic acid or its derivatives, guar gum, locust bean gum, xanthan gum, cyclodextrin, arabia gum, gellan gum, karaya gum, casein, tara gum, tamarind gum, tragacanth gum, ghatti gum, gelatin, collagen, protamine, zein, carbomer, polyacrylamide, poly vinyl acetal diethyl amino acetate, glucomannan, glucosamine, arabinogalactan, furcelleran, pullulan, polyurethane, chitosan, chitin, agar, pectin and carrageenan, the tablet, wherein
   a weight ratio of (a) metformin or its pharmaceutically acceptable salts: (b) sustained release carriers: (c) rosuvastatin or its pharmaceutically acceptable salts: (d) excipients is 1:0.01~5:0.001~0.5:0.01~5;
   metformin or its pharmaceutically acceptable salts shows sustained release patterns where it is constantly eluted in water or physiological pH dissolution medium; and
   rosuvastatin or its pharmaceutically acceptable salts shows immediate release or sustained release patterns where it is constantly eluted in water or physiological pH dissolution medium.

2. The tablet according to claim 1, wherein the said pharmaceutically acceptable salts of metformin is at least one selected from the group consisting of metformin HCl, metformin acetyl salicylic acid, metformin fumarate, metformin succinate, metformin maleate and metformin malonate.

3. The tablet according to claim 1, wherein the said pharmaceutically acceptable salts of rosuvastatin is at least one selected from the group consisting of rosuvastatin calcium, rosuvastatin HCl, rosuvastatin acetyl salicylic acid, rosuvastatin fumarate, rosuvastatin succinate, rosuvastatin maleate and rosuvastatin malonate.

4. The tablet according to claim 1, wherein the said excipient is at least one selected from the group consisting of microcrystalline cellulose, hydroxy propyl methyl cellulose, sodium carboxylmethyl cellulose, methyl cellulose, ethyl cellulose, hydroxy methyl cellulose, hydroxy ethyl cellulose, hydroxy propyl cellulose, hydroxy ethyl methyl cellulose, hydroxy ethyl ethyl cellulose, hydroxy propyl ethyl cellulose, alkyl hydroxy propyl methyl cellulose, hydroxy propyl methyl cellulose phthalate, hydroxy propyl methyl cellulose acetate succinate, cellulose acetate, cellulose acetate phthalate, polyethylene oxide, polyvinyl acetate, polyvinyl alcohol, povidone and its derivatives, corn starch, potato starch and pregelatinized starch and its derivatives, hydroxy ethyl starch, dextrin and its derivatives, dextran, maltodextrin, polydextrose, guar gum, locust bean gum, xanthan gum, cyclodextrin, arabia gum, gellan gum, karaya gum, casein, tara gum, tamarind gum, tragacanth gum, ghatti gum, gelatin, collagen, protamine, carbomer, poly acryl amide, carnauba wax, beeswax, sucrose, liquid sucrose, lactose, polyvinyl acetate, diethyl aminoacetate, polyurethane, chitosan, chitin, agar, pectin, carrageenan and shellac.

5. The tablet according to claim 1, wherein the said metformin is constantly released in water or physiological pH dissolution medium for about 2 to 24 hours.

6. The tablet according to claim 1, wherein the said 50 to 100% of rosuvastatin is immediately released in water or physiological pH dissolution medium within approximately 10 to 60 minutes.

7. The tablet according to claim 1, wherein the said rosuvastatin is constantly released in water or physiological pH dissolution medium for about 1 to 24 hours or more.

* * * * *

UNITED STATES PATENT AND TRADEMARK OFFICE
CERTIFICATE OF CORRECTION

PATENT NO. : 9,005,636 B2  
APPLICATION NO. : 13/520320  
DATED : April 14, 2015  
INVENTOR(S) : Hearan Suh et al.

Page 1 of 1

It is certified that error appears in the above-identified patent and that said Letters Patent is hereby corrected as shown below:

On the title page item (75), should read  
Inventors:

Hearan Suh  
    Myungkwan Chun  
    Taekun An  
    Juhuen Choi  
    Hyunmi Seo  
    Jisung Lim  
    Choongho Ryu  
    Jeong Ku  
    Youngdai Seo  
    Younji Shin  
    Junhee Lee  
    Gughwan An Signed and Sealed this  
Seventeenth Day of November, 2015

Michelle K. Lee  
*Director of the United States Patent and Trademark Office*